(12) United States Patent
Lipov

(10) Patent No.: US 8,987,327 B1
(45) Date of Patent: Mar. 24, 2015

(54) KITS AND METHODS FOR TREATING POST TRAUMATIC STRESS DISORDER (PTSD) AND HOT FLASHES

(71) Applicant: Eugene Lipov, Hoffman Estates, IL (US)

(72) Inventor: Eugene Lipov, Hoffman Estates, IL (US)

( * ) Notice: Subject to any disclaimer, the term of this patent is extended or adjusted under 35 U.S.C. 154(b) by 0 days.

(21) Appl. No.: 14/196,519

(22) Filed: Mar. 4, 2014

Related U.S. Application Data

(60) Provisional application No. 61/889,895, filed on Oct. 11, 2013.

(51) Int. Cl.
*A61K 31/245* (2006.01)
*A61K 31/445* (2006.01)
*A61K 31/4168* (2006.01)

(52) U.S. Cl.
CPC ........... *A61K 31/445* (2013.01); *A61K 31/4168* (2013.01); *A61K 31/245* (2013.01)
USPC ....................................................... 514/535

(58) Field of Classification Search
CPC ... A61K 31/13; A61K 31/137; A61K 31/245; A61K 31/445; A61K 31/54; A61K 31/4168; A61K 2300/00
USPC ....................................................... 514/535
See application file for complete search history.

(56) References Cited

U.S. PATENT DOCUMENTS

2006/0286131 A1 * 12/2006 Lipov ............................ 424/400

FOREIGN PATENT DOCUMENTS

WO WO 9963997 A1 * 12/1999

OTHER PUBLICATIONS

Hamner et al., "Procaine Administration and Behavioral Responsivity in Post-Traumatic Stress Disorder: A Pilot Study of Tolerability", Human Psychopharmacology, vol. 14, No. 2, pp. 105-111.*
Horrigan et al., "The Suppression of Nightmares with Guanfacine", The Journal of Clinical Psychiatry, vol. 57, No. 8, p. 371 (1996) and further in view of Dow (6,194,454 B1).*
Johnson, "Psychiatric Uses of Antiadrenergic and Adrenergic Blocking Drugs", The Journal of Nervous and Mental Disease, vol. 172, No. 3, pp. 123-132 (1984).*
Grubb et al., "Evaluation of lidocaine, xylazine, and a combination of lidocaine and xylazine for epidural analgesia in llamas", The Journal of American Veterinary Medical Association, vol. 203, No. 10, pp. 1441-1444 (1993).*
Bray RM, Pemberton MR, Lane ME, Hourani LL, Mattiko MJ, Babeu LA. Substnace use and metal health trends among US military active duty personnel: key findings from the 2008 DoD Health Behavior Survey. Mil Med 2010; 175; 390-9.

Ballenger JC, Davidson JR, Lecrubier Y, et al. Shalev AY. Consensus statement on posttraumatic stress disorder from the International Consensus Group on Depression and Anxiety. J Clin Psychiatry 2000; 61 Suppl 5: 60-6.
Tol WA, Barbui C, van Ommeren M. Management of acute stress, PTSD, and bereavement; WHO recommendations. JAMA 2013; 310; 477-8.
Department of Veterans Affairs, Uniformed mental health services in VA medical centers and clinics. VHA Handbook 1160.01 Sep. 1, 2008.
Davidson JR, Rothbaum BO, van der Kolk VA, Sikes CR, Farfel GM. Multicenter, double-blind comparison of sertraline and placebo in the treatment of posttraumatic stress disorder. Arch Gen Psychiatry 2001; 58: 485-92.
Davidson JR, Baldwin D, Stein DJ, et al. Treatment of posttraumatic stress disorder with venlafaxine extended release: a 6 month randomized controlled trial. Arch Gen Psychiatry 2006; 63: 1158-65.
Jonas DE, Cusack K, Forneris CA, et al. Psychological and Pharmacologial Treatments for Adults with Posttraumatic Stress Disorder (PTSD) Comparative Effectiveness Reviews 2013: 13EHC011 EF.
Jeffreys M, Capehart B, Friedman M. Pharmacotherapy for postraumatic stress disorder: Review with clinical applications. J Rehabil Res Dev 2012; 49: 703-15.
Chard KM, Ricksecker EG, Healy ET, Karlin BE, Resick PA. Dissemination and experience with cognitive processing therapy. J Rehabil Res Dev 2012; 49: 667-78.
Hoge CW. Interventions for war related postraumatic stress disorder: meeting veterans where they are. JAMA 2011; 306: 549-51.
Bradley R, Greene J, Russ E, Dutra L, Westen D. A multidimensional meta-analysis of psychotherapy for PTSD. The Am J of Psychiatry 2005; 162: 214-27.
Tan G, Dao TK, Farmer L, Sutherland RJ, Gevirtz R. Heart rate variability and postraumatic stress disorder; a pilot study. Appl Psychophysiol Biofeedback 2011; 36: 27-35.
Bailey CR, Cordell E, Sobin SM, Neumeister A. Recent progress in understanding the pathophysiology of post traumatic stress disorder: implications for targeted pharmacological treatment. CSN Drugs 2013: 27: 221-32.

(Continued)

*Primary Examiner* — Kevin E Weddington
(74) *Attorney, Agent, or Firm* — Howard B. Rockman; Mercedes V. O'Connor

(57) ABSTRACT

The present invention is directed to kits and methods for the treatment of a patient suffering from post-traumatic stress disorder (PTSD) and/or hot flashes by an administration of a mixture produced by a combination of a long acting local anesthetic combined with clonidine. The combination of the two pharmaceuticals produces a significant increase in duration and speed of onset of sympathetic blockade, increased intensity of the sympathetic blockage as well as the reduction of local anesthetic absorption locally. The combination significantly improves the efficacy, speed of onset and block intensity of a right sided cervical sympathetic ganglion injection (RCSGI) leading to increased length of resolution of PTSD and hot flashes as well as reducing the potential for complications related to absorption of the local anesthetic.

16 Claims, 1 Drawing Sheet

(56) References Cited

OTHER PUBLICATIONS

Blechert J, Michael T. Grossman P, Lajtman M, Wilhelm FH. Automonic and respiratory characteristics of postraumatic stress disorder and panic disorder. Psychosom Med 2007; 69: 935-43.

Lipov EG, Joshi JR, Lipov S, Sanders SE, Siroko MK. Cervical sympathetic blockage in a patient with postraumatic stress disorder, a case report. Ann Clin Psychiatry 2008; 20: 227-8.

Hickey AH, Hanling S. Pevney E, Allen R, McLay RN. Stellate Ganglion Block for PTSD. Am J Psychiatry 2012; 169: 760.

Mulvaney SW, McLean B, De Leeuw J. The use of stellate ganglion block in the treatment of panic/anxiety symptoms with combat related postraumatic stress disorder; preliminary results of long term follow up; a case series. Pain Pract 2010; 10: 349-65.

Alino J, Kosatka D, McLean B, Hirsch K. Efficacy of stellate ganglion block in the treatment of anxiety symptoms from combat related postraumatic stress disorder: a case series. Mil Med 2013; 178: e473-6.

Kapral S, Krafft P, Gosch M, Fleischmann D, Weinstabl C. Ultrasound imaging for stellate ganglion block; direct visulaization of puncture site and local anesthetic spread. A pilot study. Reg Anesth 1995; 20: 323-8.

Gofeld M, Bhatia A, Abbas S, Ganapathy S, Johnson M. Development and validation of a new technique for ultrasound guided stellate ganglion block. Reg Anesth Pain Med 2009; 34: 475-9.

Bhatia A, Flamer D, Peng PW. Evaluation of sonoanatomy relevant to performing stellate ganglion blocks using anterior and lateral simulated approaches; an observational study. Can J Anesthesia 2012; 59: 1040-47.

Shibata Y, Fujiwara Y, Komatsu T. A new approach of ultrasound guided stellate gangion block. Anesth Analg 2007; 105: 550-1.

Lee MH, Kim KY, Song JH, et al. Minimal volume of loack anesthetic required for an ultrasound guided SGB, Pain Med 2012; 13; 1381-8.

Keen SM, Kutter CJ, Niles BL, Drinsley KE. Psychometric properties of PTSD checklist in sample of male veterans.

Ruggiero KJ, Del Ben K, Scotti JR, Rabalais AE. Psychometric properties of the PTSD checklist, civilian version. J Tram Stress 2003; 16: 495-502.

Bliese PD, Wright KM, Adler AB, Cabrera O, Castrol CA, Hoge CW. Validating the primary care postraumatic stress disorder screen and the postraumatic stress disorder checklist with soldiers returning from combat. J Consult Clin Psychol 2008; 76; 272-81.

Monson CM, Gradus JL, Young Xu Y, Schnurr PP, Price AJL, Schumm JA. Change in postraumatic stress disorder symptoms; do clinicians and patients agree: Psychol Assess 2008; 20: 131-8.

Morissette SB, Woodward M, Kimbrel NA, et al. Deployment related TBI, persistent postconcussive symptoms, PTSD, and depression in OEF/OIF veterans. Rehabil Psychol 2011; 56: 340-50.

Ragsdale KA, Neer SM, Beidel DC, Frueh BC, Stout JW. Postraumatic stress disorder in OEF/OIF veterans with and without traumatic brain injury. J Anxiety Disord 2013; 27: 420-6.

Lipov E, Kelzenberg B. Sympathetic system modulation to treat post traumatic stress disorder PTSD; a review of clinical evidence and neurobiology. J Affect Disord 2012; 142; 1-5.

Liberzon I, Martis B. Neuroimaging Studies of emotional responses in PTSD. Ann NY Acad Sci 2006; 1071: 87-109.

Westerhaus MJ, Loewy AD. Central representation of the sympathetic nervous system in the central cortex. Brain Res 2001; 903: 117-27.

Smith MA. Hippocampal vulnerability to stress and aging; possible role of neurotrophic factors, possible role of neurotropic factors. Behav Brain Res 1996; 78; 25-36.

Alleva E, Petruzzi S, Cirulli F, Aloe L. NGF regulatory role in stress and coping of rodents and humans. Pharmacol Biochem Behav 1996; 54; 65-72.

Lipov EG, Joshi JR, Sanders S, Slavin KV. A unifying theory linking the prolonged efficacy of the stelate ganglion block for the treatment of chronic regional pain syndrome (CRPS), hot flashes and postraumatic stress disorder PTSD. Med Hypotheses 2009; 72: 657-61.

Takatori T, Kuroda Y, Hirose M. Local anesthetics suppress nerve growth factor, mediated neurite outgrowth by inhibition of tyrosine kinase activity of TrkA. Anesth Analg 2006; 102; 462-7.

Beckam JC, Feldman ME, Kirby AC, Atrocities exposure in Vietnam combat veterans with chronic postraumatic stress disorder; relationship to combat exposure, symptom severity, guilt and interpersonal violence. J Traum Stress 1998; 11: 777-85.

Wessely S. Twentieth century theories on combat motivation and breakdown. Jounal of Contemporary History 2006; 41: 268-86.

Marx BP, Holowka DW. PtSD disability assesment. PTSD Reearch Quarterly 2011; 22: 1-6.

Hall RC, Detection of malingered PTSD; and overview of clinical, psychometric and physiological assessment; where do we stand? J Forensic Sci 2007; 52; 717-25.

Medical Hypotheses, (2007) 69, 758-763 Stellage Ganglion Block May Relieve Hot Flashes by Interrupting the Sympathetic Nervous System.

Anesthesiology 2004; 101:488-94, Clonidine Prolongation of Lidocaine Analgesia after Sciatic Nerve Block in Rats is Mediated via the Hyperpolarization activated Cation Current, not by Adrenoreceptors.

New Options for Military Posttraumatic Stress Disorder and Suicidality, Robert N. McLay Naval Medical Center San Diego.

Anesthesiology 71:418-425, 1989, Pharmacokinetics and Dynamics of Intravenous, Intrathecal, and Epidural Clonidine in Sheep.

* cited by examiner

KITS AND METHODS FOR TREATING POST TRAUMATIC STRESS DISORDER (PTSD) AND HOT FLASHES

This application claims priority to provisional patent application Ser. No. 61/889,895, filed Oct. 11, 2013, to the extent allowed by law.

FIELD OF THE INVENTION

The present invention is directed to methods and kits for the treatment of post traumatic stress disorder (PTSD) and hot flashes by administering a right sided cervical sympathetic ganglion injection (RCSGI) for delivery of a mixture of long acting anesthetic and injectable clonidine to a patient in need of treatment for PTSD.

BACKGROUND OF THE INVENTION

Post-Traumatic Stress Disorder (PTSD) is a devastating and complex pathological anxiety condition that is characterized by severe distress and impairment in mental and physical functioning. Symptoms typically include intense anxiety, hyper-arousal, flashbacks and sleep disturbances. The impact and consequences for individuals diagnosed with PTSD include depression, substance abuse, violence, inability to maintain intimate relationships, inability to maintain parental relationships, suicide and premature mortality. PTSD is also a public health dilemma because nearly 80% of residents experience traumatic events in their lifetime. Women are twice as likely to develop PTSD symptoms than men due to the prevalence of sexual assaults.

Individuals impacted with PTSD require swift medical intervention. Current standard treatments for PTSD are pharmacotherapy and psychotherapy. Pharmaceutical treatments include selective serotonin reuptake inhibitors [SSRIs]). Treatment of PTSD is considered successful if there is a reduction in the severity, frequency and intensity of symptoms. Women tend to respond to psychotherapy and SSRI treatment, however may patients remain non-responsive or only partially responsive to such treatments, and there is no consensus on the most beneficial means of treating such patients.

Approximately 10% of PTSD affected patients seek treatment within twelve months of the PTSD stimulating traumatic event. The decision to seek treatment includes factors such as cost-benefit analysis, hesitation with psychotherapy and consideration of concerns of the side effects of SSRIs and other pharmacological agents such as nausea, tremors, nervousness and other side effects.

The occurrence of PTSD in the US military has been captured in headlines for several years. There is a marked increase in the PTSD due to the recent military operations. The number of veterans committing suicide daily has increased to 22 per day in the US, compared to the prior rate cited by the Department of Veterans Affairs at 18 per day. Possibly up to 30% of returned veterans suffer from PTSD and over 400,000 veterans receive disability benefits due to PTSD.

The cost of treatment is also to be considered, not only for the patient, but to the health care system and to communities. The costs in health care can range from $6,000 and $30,000 per year and the projected cost of disability claims alone for veterans was estimated to be $650 billion over the next 20 years. However, when a patient is not treated, this cost is immeasurable in potential loss of life through suicide and violence. The overall efficacy of PTSD treatments in the military (excluding SGB) is 25% as per report in Hoge, C. W., Interventions for War-Related Posttraumatic Stress Disorder: Meeting Vetrans Where They Are, JAMA 2011; 306:549-51.

Another health concern causing significant discomfort for many women is the occurrence of hot flashes. Although the cause of hot flashes is not well known, they occur when the blood vessels at the skin's surface dilate to cool an individual. Hot flashes can be accompanied by perspiration, rapid heart rate or chills. The severity of symptoms can vary for women, particularly those going through menopause and several factors can trigger symptoms such as caffeine, alcohol, tight clothing, spicy food and stress.

Other than avoiding triggers and some lifestyle adjustments, such as keeping cool and incorporating exercise into the routine, sufferers of hot flashes may be treated with pharmaceuticals such as birth control pills, blood pressure medicines, antidepressants and other hormone treatments. All of these treatments pose risks of side effects such as blood clots, cancers, headache, nausea, anxiety, drowsiness, tremors, diarrhea, constipation, sexual side effects and more. Due to the negative side effects of current treatments, many women opt to not be treated and suffer the symptoms of hot flashes, even for many years.

As is noted above the current treatments of PTSD and hot flashes are ineffective and the need for enhancing the reach of treatment, engagement by patients, adherence to treatment protocol, and acceptability of treatments cannot be over stated.

SUMMARY OF THE INVENTION

The methods and kits of the present invention are directed to methods and kits for the treatment of post traumatic stress disorder (PTSD) or hot flashes by administering a right sided cervical sympathetic ganglion injection (RCSGI) for delivery of a mixture of long acting anesthetic and injectable clonidine to a patient in need of treatment for PTSD or hot flashes.

The kits of the present invention minimally contain the therapeutically active ingredients of the present invention including a long acting anesthetic and clonidine. The long lasting anesthetic and clonidine may be present in the kit in two separate vials unmixed in solution or as a precipitate to be solubilized on-site prior to administration. The long lasting anesthetic and clonidine may also be present in one vial, mixed in solution or as a precipitate to be solubilized on-site prior to administration. The kit may optionally comprise a package insert on paper or on a data storage device. The kit may optionally comprise at least one syringe. The kit may optionally comprise at least one blue towel.

DETAILED DESCRIPTION

Stellate ganglion block (SGB) and right sided cervical sympathetic ganglion injection (RCSGI) offers a new treatment option for PTSD or hot flashes. SGB is a commonly used anesthetic technique that has traditionally been administered for pain relief. The injection of local anesthetic into these nerves blocks impulses, which may in turn reduce pain, swelling, color, and sweating changes in the upper extremities and may improve mobility. Stellate ganglion blocks re known as part of the treatment of Reflex Sympathetic Dystrophy (RSD), Sympathetic Maintained Pain, Complex Regional Pain Syndrome (CRPS), and Herpes Zoster (shingles) involving the head and face and/or upper extremities. Classically, SGB is an injection of cervical sympathetic ganglion at C7 and T1 levels. SGB can be administered on the left and/or right side of the neck, and the anesthetic volume used for SGB varies from 5 cc to 25 cc.

Prior treatment of PTSD by utilization of a right-sided cervical sympathetic ganglion injection (RCSGI) was called the Chicago Block (CB), more specifically, a right sided cervical sympathetic ganglion block at C-6 cervical level used for PTSD treatment, 7 cc of bupivacaine with fluoroscopic guidance. CB is different from SGB because CB is right sided only, at C6 and not C7. The long acting anesthetic is not used to control pain in the CB procedure. This use is called a "para anesthetic" application of a sympathetic block. For simplicity, the abbreviation, RCSGI, will be used in the description henceforth.

Bupivacaine and Ropivacaine have been used in the Chicago Block procedure. Most had positive results, the first placebo controlled trial was performed by the Navy and demonstrated no difference between RCSGI and placebo. This study used Ropivacaine and ultrasound guidance, not xray guidance. The Stellate Ganglia block looked promising, but it was considered to be nothing more than placebo effect by the study performed by the Navy. Preliminary data from the Navy was positive leading to the study.

Figure 2:
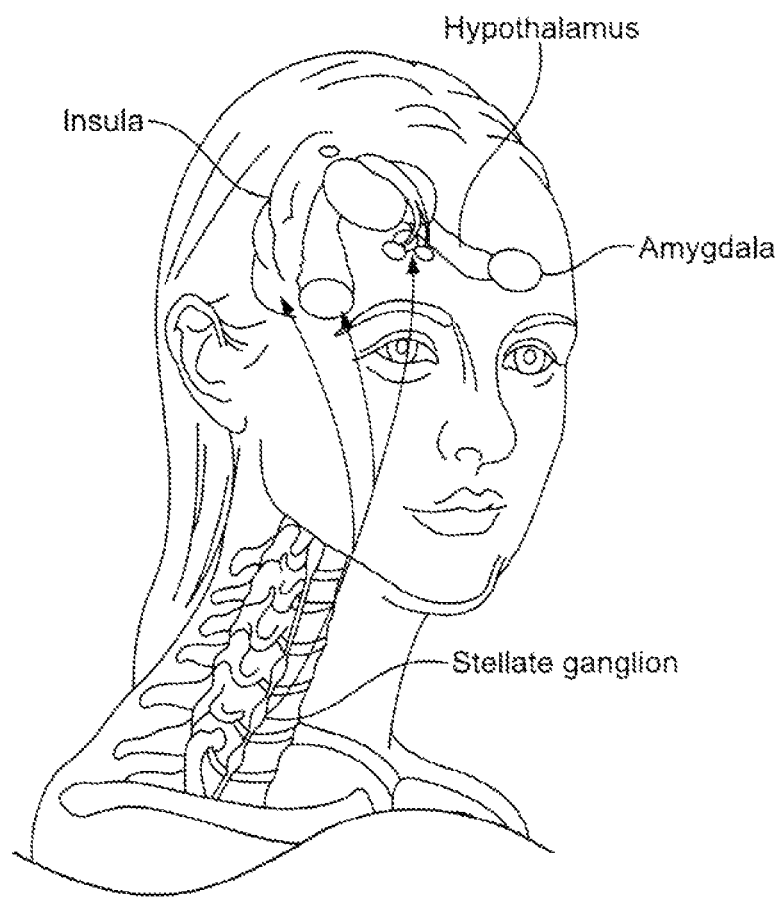
FIG. 2 demonstrates the connections from the stellate ganglion to the parts of the brain, the most relevant is he connection from Stellate ganglion to amygdala, which is the part of the brain primarily active in PTSD. Stellate is also connected to hypothalamus that controls temperature.

The present invention details the efficacy of RCSGI for treatment of PTSD based on the synaptic neurological connection from Stellate Ganglion (SG) to the part of the brain associated with PTSD, mainly amygdala and hypothalamus, as illustrated diagrammatically in FIG. 2. Stellate Ganglion connections to intra-cerebral structures have been demonstrated by the use of pseudorabies virus injections (Westerhaus and Loewy, 2001). This virus allows identification of neural pathway connections one to three synapses away from the injection site, here Stellate ganglion.

Further evidence of the sympathetic ganglion and the cerebrum connection was reported in a rat model. In this experiment specific cholinotoxin was injected in the hippocampus (HP), leading to cholinergic denervation of the HP with eventual growth of peripheral sympathetic fibers into the HP, originating from the superior cervical ganglion (Harrell LE). Thus, we believe modulation of SG can modify amygdala activity and eventually PTSD symptoms by the pathways reported above.

The second set of reports focuses on nerve growth factor (NGF) increase as a physiological response to stress. This has been reported in chronic stress by Dr. Smith (Smith, 1996) and acute stress by Dr. Alleva (Alleva et al., 1996). NGF is the best understood member of the neurotropic family, its function is to regulate a variety of signaling events such as cell differentiation and survival and apoptosis (death) of neurons (Snider, 1994). The stress modulated NGF increase is thought to activate a cascade of events eventually leading to an increase in norepinephrine (NE) levels, and leading to an increase in PTSD symptoms, as hypothesized by Dr. Lipov in 2009 (Lipov), the details are summarized below.

Intracerebral NGF increase has been shown to increase NGF concentration in the SG due to retrograde transport of NGF from the intracerebral site to the SG (Johnson et al., 1987). Next, NGF increase at the stellate ganglion has been shown to lead to sprouting (new nerve growth) at the sympathetic end terminals, which are NGF dependent (Chen et al., 2001), which in turn, cause increased norepinephrine (NE) levels. This cascade has been seen in a rat model, where infusion of NGF in the rat brain leads to an increase in NE (Isaacson and Billieu, 1996). Evidence points to NE being involved in PTSD where urine levels of NE are known to increase in PTSD (Kosten et al., 1987). Thus, it appears that trauma triggers a neurobiological cascade that ultimately leads to PTSD.

We believe this cascade is reversed by the application of a local anesthetic to the stellate ganglion, with eventual reduction of NE. This view is supported by the fact that local anesthetics suppress nerve growth factor-mediated neurite outgrowth (Takatori T), reversing the process. Further support of our theory is the report by Dr. Masataka finding that serum NE is reduced following SGB in a non-PTSD setting (Masataka Y), and significant urinary reduction of NE in 2 patients with PTSD following SGB (Lipov). Thus, as a local anesthetic is applied to the SG, PTSD symptoms may resolve. Presumably, the more NGF is reduced the more neurite growth is removed followed by reversal of PTSD to a greater degree and resulting brain changes will occur. Finally, the more intense and the longer the sympathetic block of the SG the more intense is the effect of the sympathetic block on PTSD. The mixture of a local anesthetic and clonidine is the focus of this invention and is known to produce a more intense and more prolonged sympathetic blockade.

The mixture is believed to have a more profound effect on suppression of a nerve growth factor-mediated neurite outgrowth, producing more intense reduction or removal of neurite outgrowth, reducing NE levels in the brain treating PTSD and hot flashes more effectively.

The following are injectates (substances injected) used for SGB and RCSGI:

Local Anesthetic:
Sympathetic ganglion blockade has been performed utilizing local anesthetics. Usually, long acting anesthetic has been used to have a prolonged sympathectomy (or sympathetic effect). Epinephrine may be combined with a local anesthetic to reduce local absorption of the local anesthetic and increase the length of the effect. This approach has a theoretical problem of epinephrine affecting sympathetic effect, since epinephrine is one of the agonists of the sympathetic nervous system.

Phenol:
Sympathetic ganglion blockade has been performed utilizing phenol, which is a neurolytic or a more permanent way to block a ganglion, however it is associated with significant and common complications such as persistent Horner's (droopy eye) and vocal cord nerve trauma as well as others that may be permanent.

Local Anesthetic and Steroid Combination:
The unfortunate practice of combination of steroids and local anesthetic continues without medical reason for it. This practice is associated with strokes and should not continue.

Local Anesthetic Mixed with Clonidine:
The duration and magnitude of vasodilating effect induced by sympathetic block with the addition of different concentrations of clonidine to mepivacaine was studied. In dogs, mean arterial pressure (MAP), heart rate (HR), and right as well as left brachial artery blood flow (BABF) were measured before and after stellate ganglion block (SGB) used as sympathetic block. The experimental protocol was designed as follows: 1) Group 1: left SGB using 0.5% mepivacaine 1 ml (n=6), 2) Group 2: left SGB using the addition of clonidine 0.5 microgram to 0.5% mepivacaine 1 ml (n=6), 3) Group 3: left SGB using the addition of clonidine 5 micrograms to 0.5% mepivacaine 1 ml (n=6).

The results: MAP showed no significant change throughout the study in groups 1 and 2. In group 3, MAP was lower than that of group 1. HR showed no significant change throughout the study in the three groups. Left BABF increased significantly after left SGB in the three groups. The duration of increased BABF in group 2 was the longest, and that in group 3 was the shortest among them. Right BABF after left SGB decreased significantly throughout the study in the three groups, and the magnitude of the decrease in BABF in group 3 was the highest among them. The study concluded that the sympathetic block with the addition of clonidine to local anesthetics increases both duration and magnitude of its vasodilating effect. However, sympathetic block with the addition of higher doses of clonidine to local anesthetics may induce shorter duration and lower magnitude of vasodilating effect compared with local anesthetics alone.

Although clonidine has been shown to prolong analgesia in central neuraxial blocks, its use in peripheral nerve blocks remains controversial. A systematic review was performed of the current literature to determine the benefit of adding clonidine to peripheral nerve blocks.

A systematic, qualitative review of double-blind randomized controlled trials on the benefit of clonidine as an adjunct to peripheral nerve block was performed. Studies were identified by searching PubMed (www.ncbi.nlm.nih.gov/entrez) and EMBASE (www.embase.com) databases (July 1991 to October 2006) for terms related to clonidine as an adjunct to peripheral nerve blocks. Studies were classified as supportive if the use of clonidine demonstrated reduced pain and total analgesic consumption, or prolonged block duration versus negative if no difference was found. Twenty-seven studies were identified that met the inclusion criteria. Five studies included a systemic control group. The total number of patients reviewed was 1,385. The dose of clonidine varied from 30 to 300 μg. Overall 15 studies supported the use of clonidine as an adjunct to peripheral nerve blocks with 12 studies failing to show a benefit. Based on qualitative analysis, clonidine appeared to prolong analgesia when added to intermediate-acting local anesthetics for axillary and peribulbar blocks. Clonidine improves duration of analgesia and anesthesia when used as an adjunct to intermediate-acting local anesthetics for some peripheral nerve blocks. Side-effects appear to be limited at doses up to 150 mug. Evidence is lacking for the use of clonidine as an adjunct to local anesthetics for continuous catheter techniques. Further research is required to examine the peripheral analgesic mechanism of clonidine.

In another study, a cervical sympathetic block (bupivicaine, clonidine) of a 12-15 ml solution of bupivicaine 0.5% containing 50 mcg of clonidine for cervical sympathetic block was administered in a single injection. It is unclear from the literature if clonidine, mixture with local anesthetic has a clinical effect The anesthetics of the present invention may be any short or long acting local anesthetic, or their amides or esters. Short acting anesthetics may have anesthetic effect ranging from minutes to hours on a subject being anesthetized. Long acting anesthetics may have anesthetic effect ranting from minutes to months on a subject being anesthetized. The local anesthetics may be short acting esters, such as chloroprocaine, procaine, novocaine; short acting amides such as lidocaine, prilocaine and mepivacaine; long acting esters, such as tetracaine and amethocaine; long acting amides, such as bupivicaine, levobupivacaine, ropivacaine, dibucaine and etidocine; or atypical anesthetics such as, benzocaine, cocaine, cyclomethycaine, cimethocaine, larocaine, piperocaine, propoxycaine, proparacaine, trimecaine or combinations thereof. The clonidine is used as an alpha-2-adrenergic agonist, however other active agents may also be used in the mixture with the anesthetic. Other alpha-2-adrenergic agonists that may used in the mixture of the present invention are Guanfacine, Guanabenz, Guanoxabenz, Guanethidine, Xylazine, Tizanidine, Methyldopa, Fadolmidine or Dexmedetomidine and combinations thereof.

Generally, to prepare the active pharmaceutical ingredients for administration, at least one long lasting anesthetic is mixed with clonidine in a preservative free 0.9% saline solution. Upon mixing the active pharmaceutical ingredients, the solution is pushed through a 22 micron filter and brought to desired volume with preservative free 0.9 sterile saline.

The present invention may be prepared using standard methods in the art from solubilizing and mixing the active pharmaceutical ingredients to delivery. However, by way of example the preparation may be formulated in a Class 5 sterile environment or better using an aseptic technique. A desired amount of clonidine and a long acting local anesthetic, such as bupivacaine, powders are weighed and dissolved in a minimal volume of preservative free sterile water. A sufficient amount of 0.9% preservative free (PF) sterile saline to reach 90% of the desired volume. The resultant solution may be pushed through a 0.22 micron filter of appropriate size to accommodate the total volume being prepared into a sterile syringe to be used to redistribute the final volume into the ultimate dispensing container(s). An additional volume of the 0.9% preservative free saline solution may be pushed through the same filter to establish 100% of the desired volume. New, virgin filters may be used to redistribute the pharmaceutical mixture into a new syringe or the ultimate dispensing container(s). The mixture may be transferred into sterile vials or syringes, sealed and labeled appropriately.

The kit of the present invention may comprise one vial with the active pharmaceutical ingredients solubilized, mixed, filtered and brought to volume in one vial. In another embodiment, the active pharmaceutical ingredients may be provided in separate vials either in solution, as a precipitate or in a lyophilized form for reconstitution or solubilization, filtering and bringing up to volume on-site of administration or other location.

The vials of the kit, housing the active pharmaceutical ingredients, may be glass, clear glass, amber or any other vials used in the art. The active pharmaceutical ingredients may be housed in sterile syringes that are ready for the surgical forum, or in any other housing known in the art.

The kit may optionally contain an empty or filled syringe known in the art, for use in the surgical forum. By way of examples, the syringes may be 22 g quince needle 3½ inches, 10 cc syringe labeled DYE, 10 cc syringe labeled mixture, 10 cc syringe labeled local, 2 18 gauge 1 inch needles, 1 25 gauge 1½ inch needle and the like.

The kit may also contain a package insert in any form such as paper or on a data storage device which includes specifications of the pharmaceutical ingredients, preparation instructions, dosage variations, storage instructions, administration instructions, side effects of the pharmaceutical ingredients, contraindications for administration, stability data or any other information relevant to the use of the present invention for patient care or physician information. The kit may also contain blue towels or other devices to maintain sterility. In PTSD, psychological tools such as PCL M and non-military, as well as similar tools, may be used. For hot flashes, psychological tools such as Sloan scale or equivalent, as well as a screening tool for sleep disorders may be used.

Storage instructions provided for the present invention, and for optional inclusion in the kit of the present invention, are the following: Storage at Room Temperature 15-30 C up to 24 hours; Refrigerated 2-8 C up to 3 days; or Frozen (−20 to −40 C) up to 45 days. The long acting anesthetics typically have a long shelf life sometimes up to two years and clonidine should be kept at room temperature and away from direct sunlight and moisture. A clonidine and bupivicane mixture is typically stable at room temperature for at least 90 days.

In an embodiment of the invention, the long lasting anesthetic of the present invention is bupivacaine, a white crystalline powder that is freely soluble in 95 percent ethanol, soluble in water, and slightly soluble in chloroform or acetone.

In relation to dosing, the dose administered will be dependent on the needs of each individual patient. However the long acting local anesthetic may range from 0.005 μg/cc to 40 μg/cc. In an embodiment, the anesthetic concentration may vary from 0.01% to 2% per cc. The dose of the clonidine may range from 0.5 μg/cc to 1000 μg/cc. In an embodiment, clonidine is 0.5 μg/cc. The volume of the dose administered to a patient may range from 2-50 cc. The dose administered may be approximately 7 cc. If the patient weighs between 70-100 lb, then the dose may be approximately 6 cc. If the patient weighs between 50-70 lb then the dose may be approximately 5 cc. The number of administrations may vary, but the minimum administration to see effective results to eliminate or minimize PTSD symptoms or hot flashes is one administration. Additional administrations may be administered with gaps in between administration of anywhere from 1-50 days.

Figure 1:
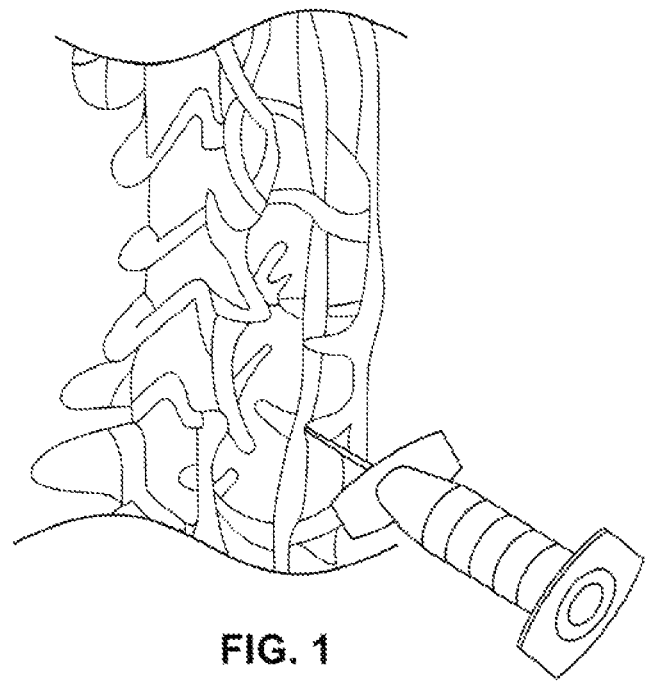
FIG. 1 is a perspective view showing various vertebrae and nerves in the neck and needle placement for right-sided cervical sympathetic ganglion injection (RCSGI).

By way of example, and not limitation, the preparation of the present invention is administered as an injectable, right sided cervical sympathetic ganglion block at C-6 cervical level. The administration may also be a left sided cervical sympathetic ganglion block at C-6 cervical level, as illustrated diagrammatically in FIG. 1. The administration of the present invention has been, and may be administered higher than C-6, for instance at C-3, on the right or left side. The administration of the present invention may also be lower than C-6, for instance at C-7, on the right or left side. The administration of the present invention may be at multiple cervical targets in the same instance of administration. The active pharmaceutical ingredients may be administered via other routes of administration known in the art such as intracerebral, epidural, topical, enteral, parenteral, intramuscular, intradermal, intravenous, subcutaneous, intrathecal and the like.

In a case study, a patient having PTSD was administered bupivicane and clonidine in a RCSGI. The first three injections were without clonidine. The fourth was with clonidine. The clonidine block began working within five minutes of the procedure and with a much stronger effect.

A 43 year old female patient was treated CB, both without clonidine and with clonidine, and reported a significantly more effective result with clonidine over the local anesthetic alone.

In a pediatric application, an 11 year old female was the first to receive an injection intended to relieve PTSD related symptoms. The procedure involved a local anesthetic mixed with clonidine delivered by a shot in the patient's neck in a procedure that is similar to an epidural given to women in labor. The anesthetic mixture blocks a substance that is called nerve growth factor which is believed to increase in PTSD patients. That condition then leads to excessive release of a hormone that triggers the "fight or flight" response in the brain. Blocking the nerve growth factor can then calm the PTSD patient, allowing the patient to get past basic survival reactions and better deal with life. The effect on the patient was immediate. This patient previously was terrified of car rides, however after this treatment slept on the car ride home. Previously the patient reported that there was no safe place in her mind, however after the treatment reported not worrying so much anymore. The objectives of the treatment were to allow the patient to sleep better, to reduce the psychiatric medications she takes and allow for her psychotherapy to be more effective. All of these objectives were accomplished after the administration of the treatment of the present invention.

Yet another patient who is a survivor of a shooting responded to the treatment described in the present invention. The shooting was at point blank range and her PTSD manifested in fright and memories as though she was being hunted down and shot again. She received the ganglion block procedure known as the Chicago Block, receiving an injection of a minute amount of local anesthetic, which was a mixture of bupivicane and clonidine. The patient reported that she can now talk about the frightening events of when she was shot.

In yet another patient, a 54 year old woman in menopause had significant improvement of her hot flashes immediately following SGB treatment. The mixture of bupivicane and clonidine was used on this patient as well.

The treatment of the instant invention intervenes when a person experiences significant anxiety and their nerve growth factor, or NGF, levels spike. That growth factor causes the stellate ganglion—a mass of nerve cells on the right side of the neck—to promote increases in the body's production of norepinephrine—a stress hormone—and kicks the body's "fight or flight". The anesthetic in the Chicago Block seems to halt the body's overproduction of NGF. When the nerve growth slows and the body stops overproducing stress hormones, a person's physical response changes.

Although preferred embodiments of the disclosure are illustrated and described in connection with particular features and formulations, the present invention can be adapted for use with a wide variety of anesthetics and pharmaceutical actives. Other embodiments and equivalents are envisioned within the scope of the claims. Various features of the disclosure have been particularly shown and described in connection with the illustrated embodiments. However, it must be understood that the particular embodiments merely illustrate the present invention, and that the invention is to be given its fullest interpretation within the terms of the claims.

What is claimed is:

1. A method for treating a patient with a medical condition selected from the group consisting of post-traumatic stress disorder and hot flashes, comprising: administering an injection of a local anesthetic and clonidine, said injection is administered at a cervical sympathetic ganglion.

2. The method of claim 1, wherein said local anesthetic is selected from the group consisting of lidocaine, mepivacaine, bupivicaine, ropivacaine and combinations thereof.

3. The method of claim 1, wherein said local anesthetic is mixed with said clonidine into a solution.

4. The method of claim 1, wherein said local anesthetic is bupivacaine.

5. The method of claim 1, wherein said injection is administered as a right sided cervical sympathetic ganglion injection.

6. The method of claim 1, wherein said injection is administered as a left sided cervical sympathetic ganglion injection.

7. The method of claim 1, wherein said injection is administered at cervical vertebrae 6.

8. The method of claim 1, wherein said injection is administered at cervical vertebrae 3.

9. The method of claim 1, wherein said injection is administered at cervical vertebrae 7.

10. The method of claim 1, wherein said local anesthetic is administered in a range from 0.005 µg/cc to 40 µg/cc.

11. The method of claim 1, wherein said clonidine is administered in a range from 0.5 to 1000 µg/cc.

12. A kit containing said local anesthetic and said clonidine of claim 1, comprising at least one vial.

13. The kit of claim 12, additionally comprising at least one syringe.

14. The kit of claim 12, additionally comprising at least one needle.

15. The kit of claim 12, additionally comprising a package insert.

16. The kit of claim 12, additionally comprising a manual for pre and post injection screening for PTSD and hot flashes diagnosis.

\* \* \* \* \*